(12) United States Patent
Guldstrand et al.

(10) Patent No.: US 9,480,445 B2
(45) Date of Patent: Nov. 1, 2016

(54) ELEVATING COLUMN AND METHOD OF CONTROLLING ELEVATION THEREOF

(71) Applicant: Solutions for tomorrow AB, Väckelsång (SE)

(72) Inventors: Mattias Guldstrand, Värends Nöbbele (SE); Martin Göran Kristoffer Yngvesson, Tävelsås (SE); Jan Bååt, Växjö (SE)

(73) Assignee: SOLUTIONS FOR TOMORROW AB (SE)

( * ) Notice: Subject to any disclaimer, the term of this patent is extended or adjusted under 35 U.S.C. 154(b) by 132 days.

(21) Appl. No.: 14/285,644

(22) Filed: May 23, 2014

(65) Prior Publication Data

US 2014/0348304 A1    Nov. 27, 2014

Related U.S. Application Data

(60) Provisional application No. 61/823,046, filed on May 14, 2013.

(51) Int. Cl.
*H05G 1/02* (2006.01)
*A61B 6/00* (2006.01)

(52) U.S. Cl.
CPC ........... *A61B 6/4405* (2013.01); *A61B 6/4452* (2013.01); *A61B 6/4482* (2013.01)

(58) Field of Classification Search
CPC .... A61B 6/44; A61B 6/4405; A61B 6/4411; A61B 6/4429; A61B 6/4435; A61B 6/4441; A61B 6/4447; A61B 6/4452; A61B 6/4458; A61B 6/4464; A61B 6/447; A61B 6/4476; A61B 6/4482

USPC ........... 248/656, 161, 162.1, 405, 414, 159, 248/157, 422, 423; 378/4, 9, 196–198
See application file for complete search history.

(56) References Cited

U.S. PATENT DOCUMENTS

| 660,868 A | * | 10/1900 | Reid | ........................ A47B 9/04 108/136 |
| 3,790,805 A | * | 2/1974 | Foderaro | .............. A61B 6/4405 378/117 |

(Continued)

FOREIGN PATENT DOCUMENTS

| JP | 2005073710 A | 3/2005 |
| WO | 9014748 A1 | 11/1990 |
| WO | 2011130203 A2 | 10/2011 |

*Primary Examiner* — Terrell McKinnon
*Assistant Examiner* — Michael McDuffie
(74) *Attorney, Agent, or Firm* — Condo Roccia Koptiw LLP (57) ABSTRACT

An elevating column for an X-ray apparatus, the X-ray apparatus preferably being mobile, wherein the column is rotationally fixed in relation to a base of the X ray apparatus, and the column having a plurality of segments, including: a first segment, having a first end and an opposite second end, arranged at the base with the first end, and a second segment having a first end and an opposite second end; wherein the second segment is arranged at its first end with an overlap of the first segment's second end and is moveable relative the first segment; and a first elevation adjustment unit including: at least a first threaded elongate member fixed at one of the first and second segments, and a first threaded receiving element arranged at the other of the first and second segments, matingly engaged with the threaded elongate member for elevation adjustment of said column.

26 Claims, 5 Drawing Sheets

(56) References Cited

U.S. PATENT DOCUMENTS

| | | | |
|---|---|---|---|
| 5,067,145 A | 11/1991 | Siczek | |
| 5,425,069 A | 6/1995 | Pellegrino | |
| 5,733,096 A * | 3/1998 | Van Doren | B25J 18/025 |
| | | | 212/296 |
| 6,052,428 A | 4/2000 | Nakano | |
| 7,185,868 B2 * | 3/2007 | Wang | A47F 5/04 |
| | | | 248/125.1 |
| 7,364,124 B2 * | 4/2008 | Yuasa | F16M 11/18 |
| | | | 248/125.8 |
| 7,581,884 B1 * | 9/2009 | Barnes | A61B 6/06 |
| | | | 378/164 |
| 7,712,389 B2 * | 5/2010 | Wang | F16H 25/20 |
| | | | 254/102 |
| 8,313,075 B2 * | 11/2012 | Kragh | A47B 9/12 |
| | | | 248/157 |
| 8,631,747 B2 * | 1/2014 | Woo | A61B 8/00 |
| | | | 108/147 |
| 2003/0190014 A1 | 10/2003 | Nakagawa | |
| 2004/0146142 A1 * | 7/2004 | Maijala | A61B 6/563 |
| | | | 378/102 |
| 2005/0236534 A1 * | 10/2005 | Bondesen | A47B 9/04 |
| | | | 248/161 |
| 2006/0120512 A1 * | 6/2006 | Watanabe | A61B 6/4405 |
| | | | 378/198 |
| 2006/0227938 A1 | 10/2006 | Walker | |
| 2010/0239073 A1 * | 9/2010 | Eaves | A61B 6/4233 |
| | | | 378/198 |
| 2010/0252697 A1 * | 10/2010 | Koenig | B66F 7/10 |
| | | | 248/161 |
| 2010/0329427 A1 * | 12/2010 | Takae | A61B 6/4283 |
| | | | 378/98.5 |
| 2011/0249807 A1 | 10/2011 | Dirisio | |
| 2011/0286575 A1 * | 11/2011 | Omernick | A61B 6/42 |
| | | | 378/62 |
| 2012/0018596 A1 * | 1/2012 | Valles Navarro | B66F 11/048 |
| | | | 248/161 |
| 2013/0064351 A1 * | 3/2013 | Urbon | A61B 6/4405 |
| | | | 378/98.5 |

\* cited by examiner

ELEVATING COLUMN AND METHOD OF CONTROLLING ELEVATION THEREOF

This application claims the benefit of U.S. Provisional Patent Application No. 61/823,046, filed May 14, 2013, the contents of which are incorporated by reference herein.

FIELD

This invention pertains in general to the field of X-ray apparatuses. More particularly the invention relates to mobile X-ray apparatuses and even more particularly to an elevating column of a mobile X-ray apparatus.

BACKGROUND

An elevating column has been disclosed in US2011/0249807 A1, which column enables imaging lower than usual. However, although the range may have been improved, imaging can still not be performed close to the floor. Furthermore, although the apparatus disclosed may be put into a compact shape, it is still heavy. One of the reasons for it being heavy is that a counter-weight is used. Moreover, the elevating column has many components and is thus complicated in its construction. Therefore also control of it may be complicated. In addition, with the counter-weight drive mechanism of the apparatus it may be difficult to obtain sufficient accuracy. Further, it may also be difficult adjusting the elevation fast enough.

Thus, there may be a need for an elevating column with an increased range of reach towards the floor. There may also be a need for a lighter and/or more compact apparatus. Furthermore, there may be a need for a simpler elevating column with fewer components. Moreover, there may be a need for an elevating column, which is simple in construction and/or easy to control. In addition, there may be a need for elevation adjustments with a higher accuracy and/or faster elevation adjustments.

SUMMARY

Accordingly, embodiments of the present invention preferably seek to mitigate, alleviate or eliminate one or more deficiencies, disadvantages or issues in the art, such as the above-identified, singly or in any combination by providing an elevating column and methods related thereto, according to the appended patent claims.

According to aspects of the invention, an elevating column and methods related thereto are disclosed, whereby elevation adjustments are made with sufficient accuracy and speed.

According to one aspect of the invention, an elevating column for an X-ray apparatus is provided. The X-ray apparatus is mobile. The column is preferably rotationally fixed in relation to a base of the X-ray apparatus. The column has a plurality of segments, including a first segment, which has a first end and an opposite second end. Furthermore, the first segment is arranged at the base with the first end. The column also has a second segment, which has a first end and an opposite second end. Furthermore, the second segment is arranged at its first end with an overlap of the first segment's second end. Moreover the second segment is moveable relative the first segment. The column further includes a first elevation adjustment unit, which unit includes at least a first threaded elongate member fixed at one of the first and second segments. The first elevation adjustment unit also includes a first threaded receiving element arranged at the other of the first and second segments, matingly engaged with the threaded elongate member.

According to another aspect of the invention, a method of controlling elevation of the elevating column is provided. The method includes receiving information from position sensors. Furthermore, the method includes sending a first control signal to a first electrical motor. Moreover, an elevation of a moveable second segment of the elevating column is controlled with the first electrical motor by actuating a rotational movement of either a first threaded receiving element or a first threaded elongate member of a first elevation adjustment unit. A second control signal is sent to a second electrical motor.

Furthermore, an elevation of a connecting segment, attached to a telescopic arm, of the elevating column is controlled with a second electrical motor by actuating a rotational movement of either a second threaded receiving element or a second threaded elongate member of a second elevation adjustment unit.

According to yet another aspect of the invention, a method of preparing a mobile X-ray apparatus for transport is provided. The method includes controlling elevation of a moveable second segment of an elevating column to a lowest possible position with a first electrical motor. The elevation control is performed by actuating a rotational movement of either a first threaded receiving element or a first threaded elongate member of a first elevation adjustment unit.

The method also includes controlling elevation of a connecting segment, comprising an outer part and an inner part attached to a telescopic arm, of the elevating column to a highest possible position with a second electrical motor. Moreover, the elevation control of the connecting element is performed by actuating a rotational movement of either a second threaded receiving element or a second threaded elongate member of a second elevation adjustment unit.

Furthermore, the method includes rotating the outer part horizontally around the inner part until a telescopic arm of the apparatus is positioned on top of a base of the apparatus. In addition, the method may include controlling elevation of the connecting segment by lowering it until the telescopic arm is positioned in a locking position, such as in a hollow space of the base.

Further embodiments of the invention are defined in the dependent claims, wherein features for the second and subsequent aspects of the invention are as for the first aspect mutatis mutandis.

Some embodiments of the invention provide for high precision elevation adjustments.

Some embodiments of the invention also provide for that the operating elevation range of the telescopic arm and the range for image capturing is extended towards very low positions, thus enabling capturing of images at very low positions.

Some embodiments of the invention also provide for that fast and easy rotation with high precision is obtained.

Some embodiments of the invention also provide for aster vertical movement of the column, e.g. if both the second and the connecting segments are operated simultaneously.

Some embodiments of the invention also provide for that the mobile apparatus is easy to transport due to e.g. a compact size and an increased visibility.

Some embodiments of the invention also provide for that the elevation adjustment is split between adjusting the second segment and adjusting the connecting segment.

Some embodiments of the invention also provide for that precision and/or speed of elevation adjustment may be increased.

Some embodiments of the invention also enable movement of the connecting segment in opposite direction as movement of the moveable second segment.

Some embodiments of the invention also provide for an increased stability and avoidance of wobbling of the first threaded elongate member and thus an increase in precision, reliability, safety and life span of the threaded elongate member, the first elevation adjustment unit and the system may be achieved.

Some embodiments of the invention also provide for that the moveable second segment can be height adjusted fast whereas the connecting segment can be used for alignment with high precision. Thus, an increase in adjustment speed and adjustment precision may be achieved at the same time.

Some embodiments of the invention also provide for an extension of the range of reach with the X-ray tube towards the floor.

Some embodiments of the invention also enable the use of larger front wheels, which improves steering, transportation properties and precision.

Some embodiments of the invention also provide for optimization of the range of reach, or optimization of the highest possible point, while maintaining a compact size during transportation.

Some embodiments of the invention also provide for reduction of the number of components, since a sufficient range of reach and a sufficiently high highest possible point can be achieved with only two segments, i.e. the first and second segments, as opposed to three or more.

Some embodiments of the invention also provide for that space inside the column is freed up.

Some embodiments of the invention also provide for that the column may be made smaller, i.e. with a smaller circumference or cross section. Thus the weight may be lowered.

Some embodiments of the invention also provide for that the center of gravity may be made lower, e.g. if the motor is positioned outside the column and attached to the base instead of inside the column.

Some embodiments of the invention also provide for thinner walls of the column and thus lower weight.

Some embodiments of the invention also provide for an improved stability of the column.

Some embodiments of the invention also enable a compact size during transportation, and thus enable the use of a smaller vehicle, such as a van for transportation.

Some embodiments of the invention also provide for a lower weight of the X-ray apparatus. Thus, it may be easier to transport the apparatus with e.g. a van or another small vehicle instead of transporting it with a truck, and therefore lower fuel consumption and cheaper transportation may be achieved. This may be important if the mobile X-ray apparatus is transported to the patients instead of transporting the patients to an X-ray apparatus.

Some embodiments of the invention also provide for a fast and easy control of elevation of the elevating column and/or the arm.

Some embodiments of the invention also provide for that the speed of adjustment can be increased.

Some embodiments of the invention also provide for a lighter apparatus, since the rotation hub may be made smaller and lighter, since the load may be made smaller due to e.g. the use of a rotationally fixed segment of the column.

Some embodiments of the invention also enable the use of a recessed placement of the column and therefore an extension of the range of reach with the X-ray tube to very low positions and/or space for larger front wheels and/or placement of the motor associated with one of the segments of the column outside the column.

It should be emphasized that the term "includes/including" when used in this specification is taken to specify the presence of stated features, integers, steps or components but does not preclude the presence or addition of one or more other features, integers, steps, components or groups thereof.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a mobile X-ray apparatus and in particular to an elevating column of a mobile X-ray apparatus. However, it will be appreciated the invention is not limited to this application but may be applied to many other X-ray apparatuses including for example stationary X-ray apparatuses.

Figure 6:
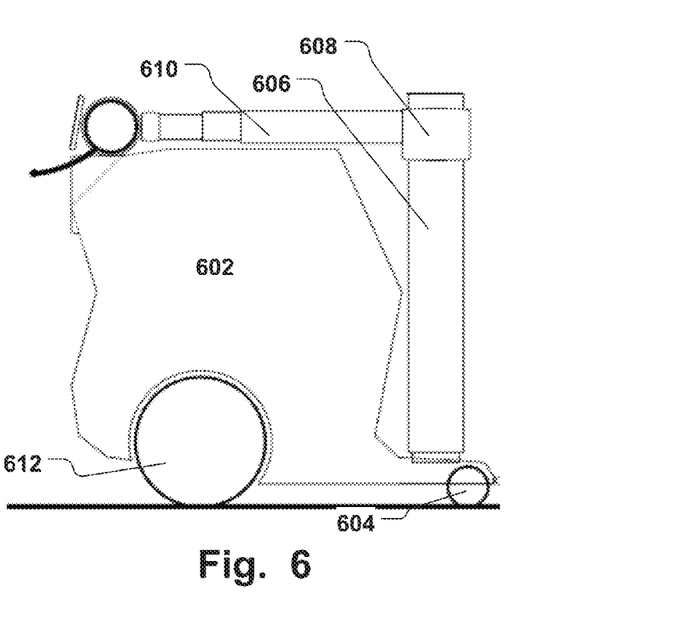
FIG. 6 is a lateral view of a mobile X-ray apparatus.

FIG. 6 shows a mobile X-ray apparatus 600. The X-ray apparatus 600 has a base 602 and an elevating column 606. The base 602 has at least one front wheel 604 and at least one rear wheel 612. Preferably the base 602 has two front wheels and two rear wheels. The front wheels are in this embodiment large, e.g. larger than the normal size of front wheels for mobile X-ray apparatuses and preferably having a diameter which is larger than 12 cm. However, in other embodiments, the front wheels are smaller than the normal size of front wheels for mobile X-ray apparatuses and preferably having a diameter which is smaller than 6 cm. An arm 610 for an X-ray tube, which arm 610 may be telescopic, is attached to the column 606 via a connecting segment 608.

Figure 1A:
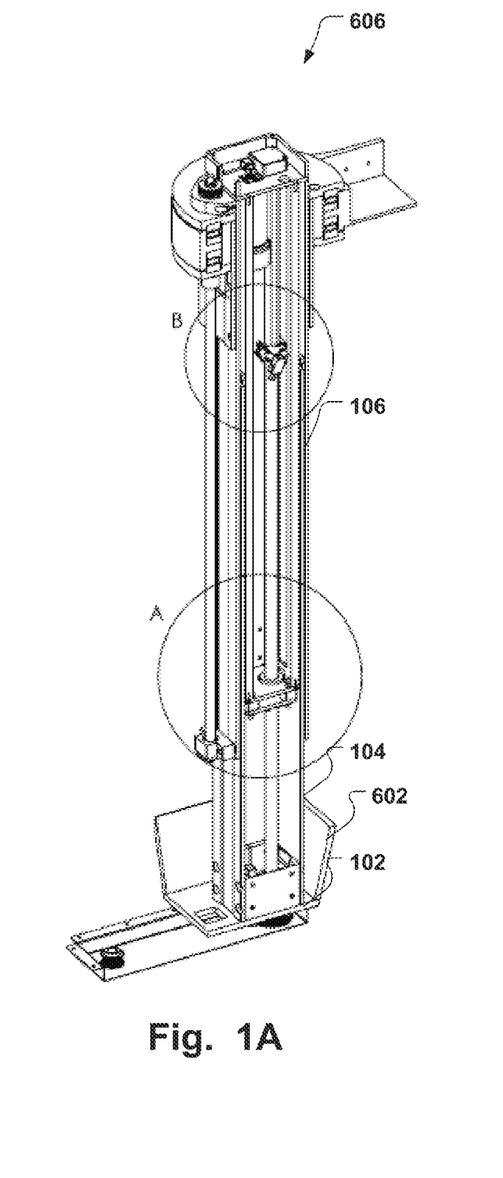
FIG. 1A is a perspective view of an elevating column.

In an embodiment of the invention according to FIG. 1A, which is a perspective view of an elevating column 606, the elevating column 606 has a second segment 106, which is moveable, preferably vertically, in relation to a first segment 104. Thus, the elevating column 606 is in this embodiment rotationally fixed in relation to the base 602 of the X-ray apparatus 600. However, in other embodiments, the elevating column may move in a rotational direction in relation to the base 602.

The column 606 has a plurality of segments. It has a second segment 106 having a first end and an opposite second end. The second segment 106 is positioned with the first end at the top and with the opposite second end at the bottom. Furthermore, the column 606 has a first segment 104, which has a first end and an opposite second end. The first segment 104 is positioned with the first end at the bottom and with the opposite second end at the top. Furthermore, the first segment 104 is arranged at the base 602 with the first end. In one embodiment, the first segment is attached to and fixed to a recess 102 of the base 602, i.e. the base 602 is provided with a recess 102. A first end of the first segment 104 of the column 606 is fixed to the base 602 at the recess 102 and recessed into the recess 102. Thus, the range of reach with the X-ray tube may be extended towards the floor and enable the use of larger front wheels, which improves steering, transportation properties and precision. Furthermore, optimization of the range of reach or the highest possible point with a maintained compact size during transportation may be achieved. Moreover, reduction of the number of components may be achieved, since a sufficient range of reach and a sufficiently high highest possible point can be achieved with only two segments, i.e. the first and second segments, as opposed to three or more segments. Thus, in this embodiment, the front wheels are preferable large.

However, in another embodiment, the first segment is attached to and fixed directly to the base 602, i.e. the base has no recess 102.

The second segment 106 is arranged at its first end with an overlap of the first segment's second end and is moveable relative the first segment 104.

Figure 1B:
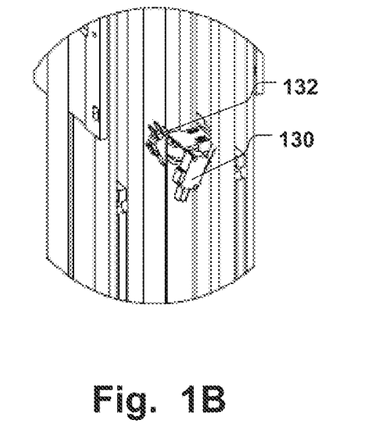
FIG. 1B is a perspective detail view of limit switches of an elevating column.
Figure 1C:
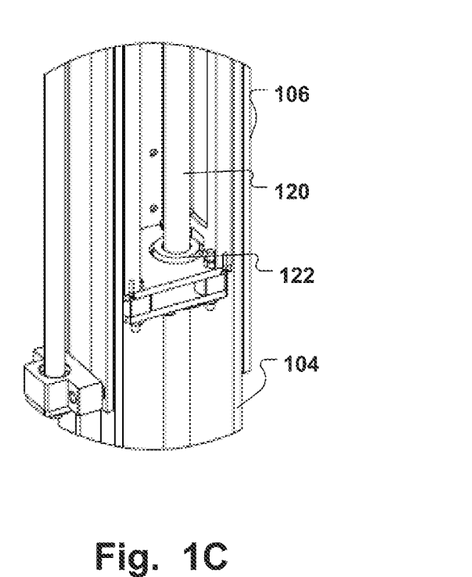
FIG. 1C is a perspective detail view of some parts of an elevation adjustment unit for an elevating column.

Furthermore, as can be seen from FIG. 1c, the column 606 further has a first elevation adjustment unit, which is adapted to adjust the elevation of the moveable second segment 106. The first elevation adjustment unit has at least a first threaded elongate member 120. In a first embodiment, the first threaded elongate member 120 is fixed at the first segment 104. In this embodiment, a first threaded receiving element 122 is arranged at the second segment 106, matingly engaged with the threaded elongate member 120.

In a second embodiment, the first threaded elongate member 120 is fixed at the second segment 106. In this embodiment, a first threaded receiving element 122 is arranged at the first segment 104, matingly engaged with the first threaded elongate member 120.

In other embodiments, the first elevation adjustment unit has a plurality of threaded receiving elements and threaded elongate members.

With the use of a first elevation adjustment unit, high precision elevation adjustments may be obtained.

From FIG. 1B position sensors such as limit switches 130, 132 of an elevating column can be seen. Furthermore, the elevating column may have other position sensors. The position sensor may be any device that permits position measurement. Thus, the position sensors may be any of capacitive transducers, capacitive displacement sensors, eddy-current sensors, ultrasonic sensors, grating sensors, Hall effect sensors, inductive non-contact position sensors, Laser Doppler Vibrometers, linear variable differential transformers, multi-axis displacement transducers, photo-diode arrays, piezo-electric transducers, proximity sensors, rotary encoders, seismic displacement pick-up sensors or string potentiometers. However, preferably the position sensors are absolute position sensors, such as absolute linear sensors.

Figure 2A:
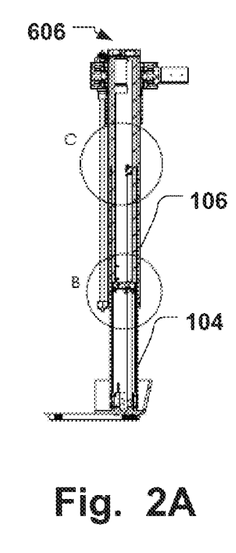
FIG. 2A is a lateral view of an elevating column.

In FIG. 2A the elevating column 606 is in a position, in which the second segment 106 has been adjusted to a certain height position. From this height position it is possible to move the second segment 106 down or up. Thus, the height position in this figure is an intermediate position.

Figure 2B:
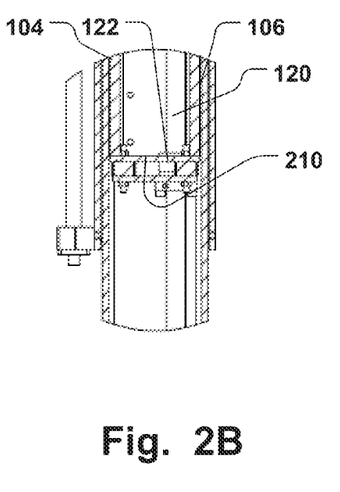
FIG. 2B is a lateral detail view of some parts of an elevation adjustment unit for an elevating column.

From FIG. 2B some parts of the elevation adjustment unit can be seen. The elevation adjustment unit has in this embodiment a first threaded receiving element 122 and a first threaded elongate member 120. The first threaded receiving element 122 may be a nut, a nut-shaped element or an elongated hollow rod with an internal thread and the first threaded elongate member 120 may be one or more rods with external threads. The first threaded receiving element 122 is in this embodiment fixed to the first segment 104 with a bracket 210. The elevation adjustment is in this embodiment made by actuating a rotational movement of the first threaded elongate member 120 with a motor. The motor may be any type of motor, but preferably an electrical motor, such as a Permanent-magnet Direct Current (PMDC) motor or a Brushless Direct Current (BLDC) motor. Other motors that can be used are AC motors or DC motors, such as Induction Motors, Wound Rotor Motors, linear motors or stepper motors.

In another embodiment, the first threaded elongate member 120 may be fixed in a rotational direction and the elevation adjustment performed by actuating a rotational movement of the first threaded receiving element 122 with a motor, preferably an electrical motor, such as a Permanent-magnet Direct Current (PMDC) motor or a Brushless Direct Current (BLDC) motor.

Figure 2C:
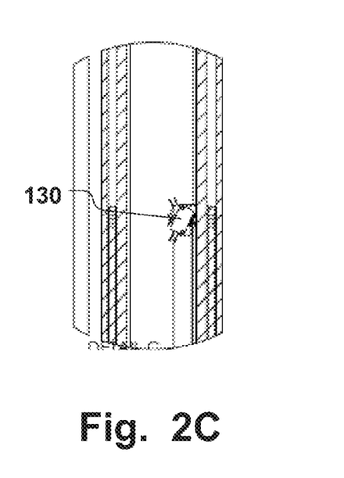
FIG. 2C is a lateral detail view of limit switches of an elevating column.
Figure 2D:
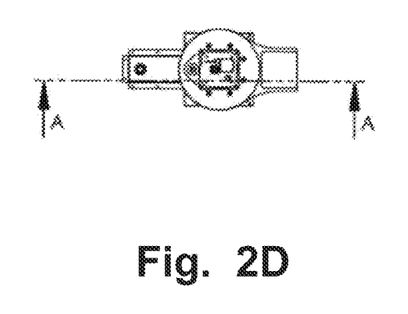
FIG. 2D is a top view of an elevating column.

FIG. 2C shows a position sensor of the elevating column. The position sensor in this figure is a limit switch 130. However, also other types of position sensors may be used. Each position sensor gives an indication, preferably an electrical signal, which can be converted to a position and/or a height of the second segment 106 and/or of the column 606.

Figure 3A:
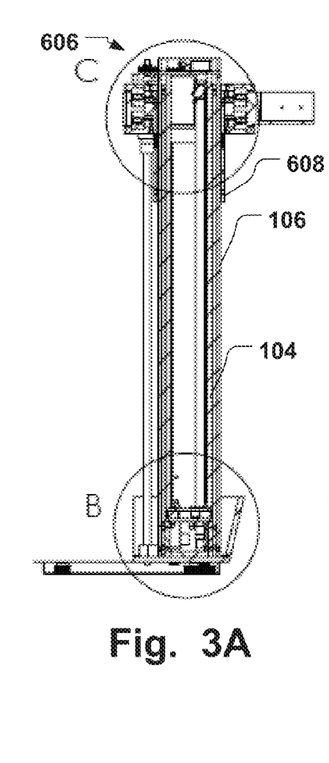
FIG. 3A is a lateral view of an elevating column with segments, while a moveable second segment is in its least extended position.
Figure 3B:
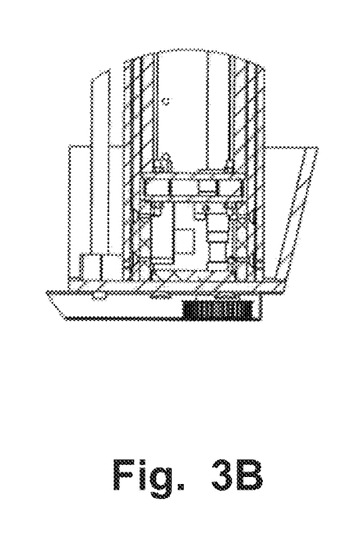
FIG. 3B is a lateral detail view of some parts of an elevation adjustment unit for an elevating column with segments, while a moveable second segment is in its least extended position.

FIG. 3A shows the elevating column with segments, while the moveable second segment 106 is in its least extended position and the connecting segment 608 is in its highest position. This is the preferred position of the elevating column during transportation of the mobile X-ray apparatus, since the visibility is increased by having the column in an as low position as possible and since the mobile X-ray apparatus is put into an as compact size as possible by positioning the arm 610 on top of the base 602 during transportation.

The connecting element 608 is connected to the second segment 106 and located radially outside the moveable second segment 106. Since the connecting segment 608 is moveable radially outside the second segment 106 in a vertical direction, the operating elevation range of an arm 610 attached to the connecting element 608 and of image capturing is extended towards very low positions, thus enabling capturing of images at very low positions.

Figure 3C:
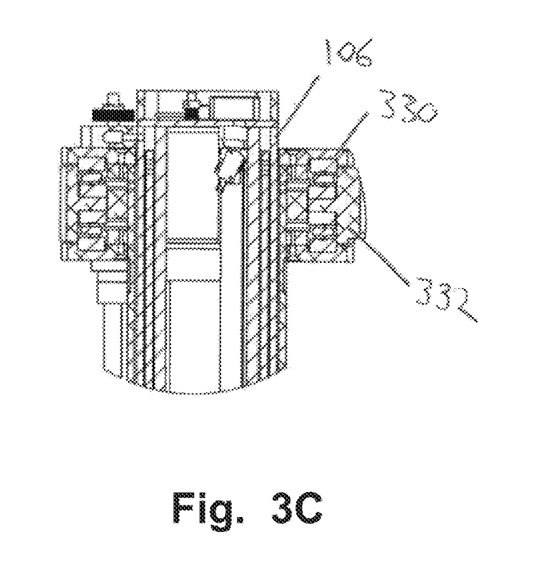
FIG. 3C is a lateral detail view of limit switches of an elevating column with segments, while a moveable second segment is in its least extended position.

As can be seen from FIG. 3c, the connecting segment 608 has an inner part 330 connected to the moveable second segment 106 and an outer part 332 connected to the arm 610, which may be telescopic. The outer part 332 is rotatable horizontally around the inner part 330. Thus, the arm 610 may be rotated into an appropriate position and fast and easy rotation of the arm 610 with high precision may be obtained.

Figure 4A:
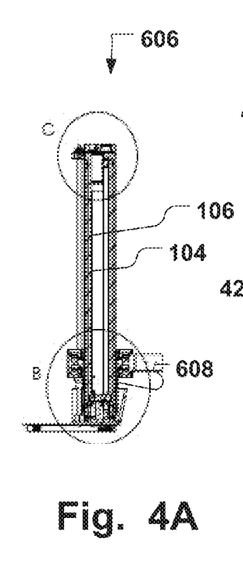
FIG. 4A is a lateral view of an elevating column with segments, while a moveable second segment is in its least extended position and a connecting segment is in its lowest position.

FIG. 4A is another view of the elevating column with segments. In this figure, the moveable second segment 106 is in its least extended position, i.e. in the lowest position. Also the connecting segment 608 is in its lowest position. Thus, with the segments in these positions the reach of an X-ray tube attached to the arm 610, which is attached to the column 606 via a connecting segment 608, is extended to very low positions close to the floor.

The connecting segment 608, which is located radially outside the second segment 106, is moveable in a rotational direction around the second segment 106. Therefore an arm 610 attached to the connecting segment 608 may be rotated into an appropriate position for capturing of X-ray images. Furthermore, the connecting segment 608 is moveable in a vertical direction along the second segment 106.

Figures 4B, 4C:
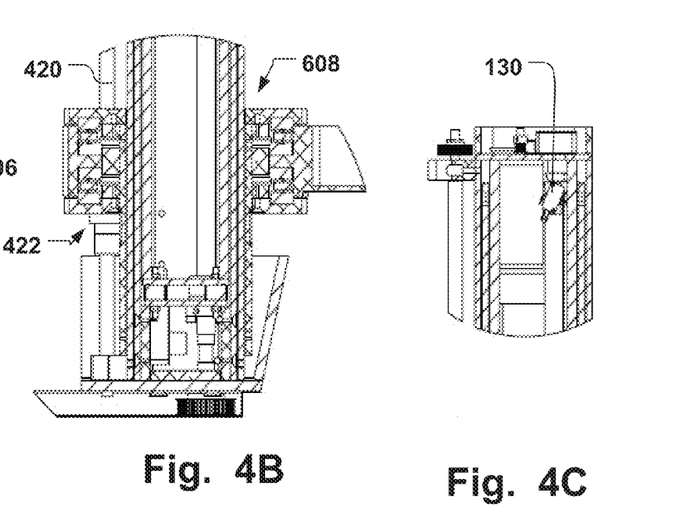
FIG. 4B is a lateral detail view of some parts of an elevation adjustment unit for an elevating column with segments, while a moveable second segment is in its least extended position and a connecting segment is in its lowest position.
FIG. 4C is a lateral detail view of limit switches of an elevating column with segments, while a moveable second segment is in its least extended position and a connecting segment is in its lowest position.

From FIG. 4B, some parts of a second elevation adjustment unit, which is adapted to adjust the elevation of the connecting segment 608, can be seen. The second elevation adjustment unit has in this embodiment a second threaded receiving element 422 and a second threaded elongate member 420. The second threaded receiving element 422 may be a nut, a nut-shaped element or an elongated hollow rod with an internal thread and the second threaded elongate member 420 may be a rod with an external thread. The second threaded receiving element 422 is in this embodiment fixed to the connecting segment 608 in a rotational direction or in all directions. The second threaded elongate member 420 is positioned outside the second segment 106 and attached to the second segment 106 at the bottom and the top. E.g. the second threaded elongate member 420 has a first end and an opposite second end. Furthermore, the second threaded elongate member 420 is positioned outside and in parallel with the second segment 106. Thus the first end of the second threaded elongate member 420 is positioned at the first end of the second segment 106 and the second end of the second threaded elongate member 420 is positioned at the second end of the second segment 106.

Alternatively, the threaded elongate member 420 may be positioned inside the second segment 106, e.g. if there is a slot in the second segment 106 and/or the second segment 106 may be used as a cover for the threaded elongate member 420.

The elevation adjustment is in this embodiment made by actuating a rotational movement of the second threaded elongate member 420 with a motor. The motor may be any type of motor, but preferably an electrical motor, such as a Permanent-magnet Direct Current (PMDC) motor or a Brushless Direct Current (BLDC) motor. Other motors that can be used are AC motors or DC motors, such as Induction Motors, Wound Rotor Motors, linear motors or stepper motors.

In this embodiment, the second threaded receiving element 422 is arranged at the connecting segment 608 and fixed thereto. It is matingly engaged with the threaded elongate member 420.

In another embodiment, the second threaded elongate member 420 may be fixed in a rotational direction and the elevation adjustment performed by actuating a rotational movement of the second threaded receiving element 422 with a motor, preferably an electrical motor, such as a Permanent-magnet Direct Current (PMDC) motor or a Brushless Direct Current (BLDC) motor. The motor is preferably positioned inside the moveable second segment 106. In this embodiment, the second threaded elongate member 120 is fixed at the connecting segment 608. Furthermore, in this embodiment, a second threaded receiving element 122 is arranged at the second segment 106, matingly engaged with the second threaded elongate member 420.

By the use of a first and a second elevation adjustment unit, elevation adjustment is split between adjusting elevation of the second segment 106 and adjusting elevation of the connecting segment 608. Thus, faster elevation adjustments and/or elevation adjustments with higher precision may be achieved.

A control unit may be used for calculating a first, a second and/or a total amount of elevation adjustment. The calculations of these amounts may be based on a measured present elevation of the connecting element 608 and/or the second segment 106. Furthermore the calculations may also be based on a reference value or a desired value, which may be preset or supplied by the user. The control unit may also be used to control a second actuator, such as a second electrical motor, to make the second elevation adjustment unit move the connecting segment 608 to an elevation depending on the second amount of elevation adjustment. Furthermore, the control unit may be used to control a first actuator, such as a first electrical motor, to make the first elevation adjustment unit move the second segment 106 to an elevation depending on the first amount of elevation adjustment. Thereby precision and/or speed of elevation adjustment may be increased. With this arrangement, it is also possible to operate and move the connecting segment 608 in an opposite direction as movement of the moveable second segment 106. This will be the case when one of the first and second amounts of elevation adjustment is negative and the other of the first and second amounts of elevation adjustment is positive.

Furthermore, the first actuator or electrical motor may be fixed to the base. It may be located at a distance from the elevating column 606. Moreover, it may be connected to the first elevation adjustment unit with a chain, cable or a belt. Thus, space inside the column 606 is freed up and can be used for other purposes. Furthermore, the column may be made smaller, i.e. with a smaller circumference or cross section. Moreover, the center of gravity may be made lower with the motor outside the column 606 instead of inside the column 606. Thus the weight may be lowered.

From FIG. 4C a limit switch 130 of the elevating column 606 can be seen. Furthermore, the elevating column 606 may also have position sensors. The moveable second segment 106 is in this figure in its least extended position and the connecting segment 608 in its lowest position. Since the connecting segment 608 is in its lowest position, it should not be able to move any lower. This can be ensured by having some kind of stop plates or limit switches 130, 132, which ensures that the connecting segment 608 cannot move past a lowest and/or highest position. Alternatively, or in addition, the connecting segment 608 may be controlled to move only within a certain range of movement and automatically stop when the position measured with position sensors (not shown) reaches a lowest or highest allowed value. Such a control can be made with a control unit, which sends signals to the movement actuators. The movement of the second segment 106 may be controlled the same way or in a similar way. The control of movement of the second segment 106 may then utilize information retrieved from the position sensors. Furthermore, the second and first threaded elongate members may have automatic braking properties.

Figure 5A:
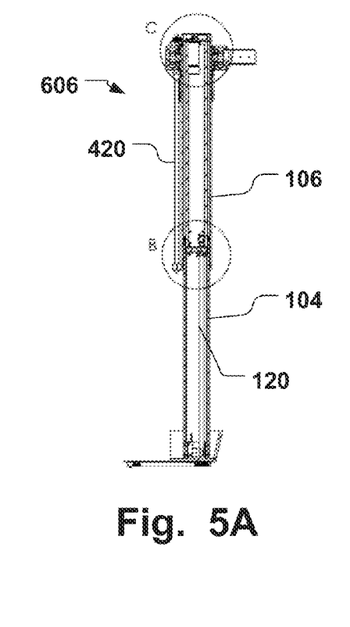
FIG. 5A is a lateral view of an elevating column with segments, while a moveable second segment is in its most extended position and a connecting segment is in its highest position.
Figure 5B:
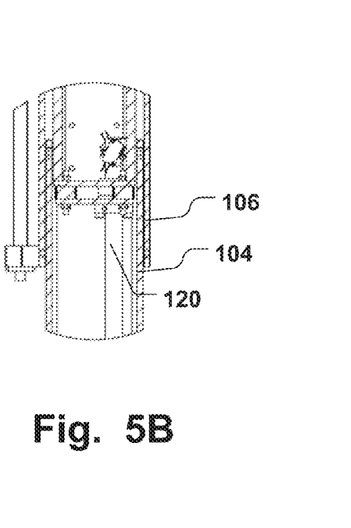
FIG. 5B is a lateral detail view of some parts of an elevation adjustment unit for an elevating column with segments, while a moveable second segment is in its most extended position and a connecting segment is in its highest position.
Figure 5C:
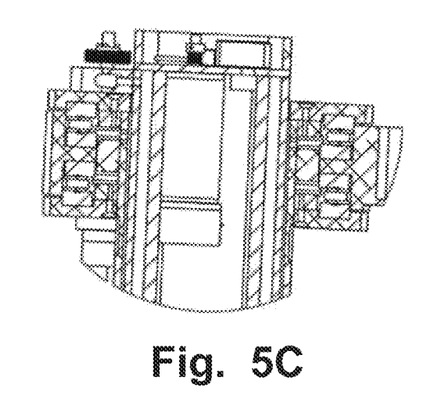
FIG. 5C is a lateral detail view of limit switches of an elevating column with segments, while a moveable second segment is in its most extended position and a connecting segment is in its highest position.

As can be seen from FIGS. 5A and 5B, the first threaded elongate member 120 has a first end and an opposite second end. The first threaded elongate member 120 is positioned inside the first segment 104 so that the first end of the first threaded elongate member 120 is positioned at the first end of the first segment 104 and the second end of the first threaded elongate member 120 is positioned at the second end of the first segment 104. In this embodiment, a u-shaped profile is attached to and positioned inside the second segment 106. Furthermore, the first threaded receiving element 122 is fixed to the u-shaped profile. The use of the u-shaped profile increases stability and avoids wobbling of the first threaded elongate member 120 and thus increases precision, reliability, safety and life span of the threaded elongate member 120, the first elevation adjustment unit and the system.

Alternatively, the first threaded elongate member 120 is positioned inside the second segment 106 so that the first end of the first threaded elongate member 120 is positioned at the first end of the second segment 106 and the second end of the first threaded elongate member 120 is positioned at the second end of the second segment 106. In this embodiment, a u-shaped profile is attached to and positioned inside the first segment 104. Furthermore, the first threaded receiving element 122 is fixed to the u-shaped profile.

In one embodiment, a pitch or lead of an internal thread of the second threaded receiving element 422 and an external thread of the second threaded elongate member 420 is larger than a pitch or lead of an internal thread of the first threaded receiving element 122 and an external thread of the first threaded elongate member 120, with e.g. a factor of 2. Thus, the moveable second segment can be height adjusted fast and the connecting segment can be used for alignment with high precision.

Furthermore, the second segment 106 and/or the first segment 104 may comprise four complete walls arranged in a rectangular or square formation cross-sectionally. The walls may be made without any slots and consequently the walls may be made thinner than if slots had been present. Thus the weight may be lowered and/or the stability of the column 606 improved. Alternatively, at least one of the walls may have at least one slot.

Moreover, the elevating column 606 may be operated without a counter-weight. This enables a compact size during transportation, and thus enables the use of a smaller vehicle, such as a van for transportation. Therefore cheaper transportation and lower fuel consumption may be achieved.

In one embodiment, the overlap of the second and first segments 106, 104, when the column 606 is set to a highest position, is optimal and within 10-20 cm, and preferably within 15-17 cm.

In another embodiment, a ratio between an overlap of the second and first segments 106, 104, when the column 606 is set to a highest position, and a maximum height above the floor of the column 606 is below 0.1 and preferably below 0.075.

In yet another embodiment, a length of the second segment 106 and a length of the first segment 104 are selected so that a span between a lowest possible position and a highest possible position of the elevating column 606 is optimized and at least 1.5 m, and preferably at least 1.7 m.

Figure 7:
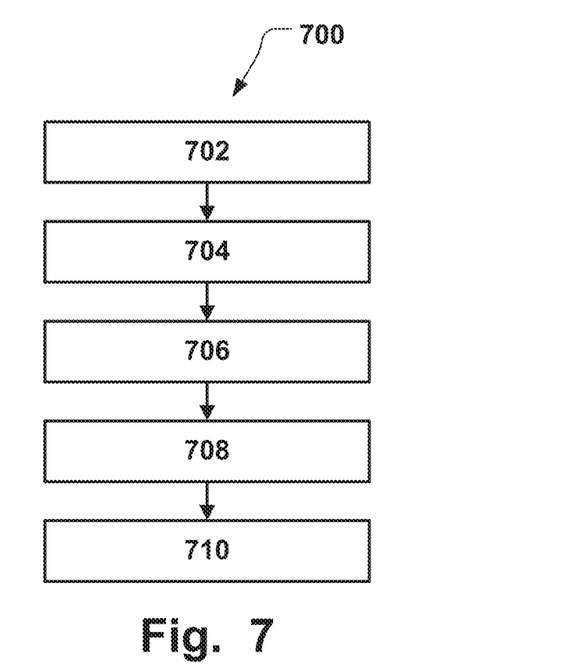
FIG. 7 illustrates steps of a method of controlling elevation of an elevating column.

FIG. 7 shows some steps of a method 700 of controlling elevation of the elevating column 606. From this figure it can be seen that an elevation of a moveable second segment 106 of the elevating column 606 is controlled 706 with a first actuator, such as a first electrical motor, e.g. a Permanent-magnet Direct Current (PMDC) motor or a Brushless Direct Current (BLDC) motor. A first control signal is sent 704 from a control unit, which has received 702 information from position sensors, to the first actuator. The first actuator actuates a rotational movement of either a first threaded receiving element 122 or a first threaded elongate member 120 of a first elevation adjustment unit. Thus, the actuator actuates an elevation adjustment of the second segment 106.

Furthermore, an elevation of a connecting segment 608, which is preferably attached to a telescopic arm 610, of the elevating column 606 is controlled 710 with a second actuator, such as a second electrical motor, e.g. a Permanent-magnet Direct Current (PMDC) motor or a Brushless Direct Current (BLDC) motor. A second control signal is sent 708 from a control unit, which has received 702 information from position sensors, to the second actuator. The second actuator actuates a rotational movement of either a second threaded receiving element 422 or a second threaded elongate member 420 of a second elevation adjustment unit. Thus, the second actuator actuates an elevation adjustment of the connecting segment 608.

With this method, a fast and easy control of the elevation of the elevating column 606 may be achieved. The elevation of the moveable second segment 106 and the elevation of the connecting segment 608 are in one embodiment controlled simultaneously. Thus, the speed of adjustment may be increased.

Figure 8:
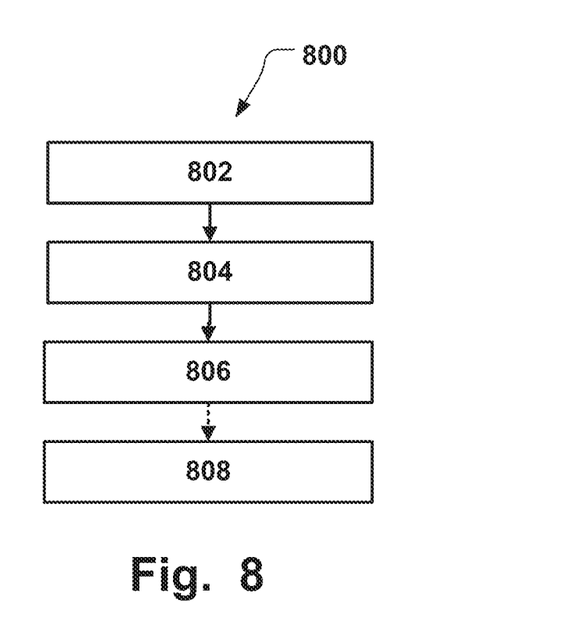
FIG. 8 illustrates steps of a method of preparing a mobile X-ray apparatus for transport.

FIG. 8 shows some steps of a method 800 of preparing a mobile X-ray apparatus for transport. In 802, control of elevation of a moveable second segment of an elevating column to a lowest possible position with a first actuator, such as a first electrical motor, e.g. a Permanent-magnet Direct Current (PMDC) motor or a Brushless Direct Current (BLDC) motor, is performed. A first control signal is sent from a control unit, which may have received information from position sensors, to the first actuator. The first actuator actuates a rotational movement of either a first threaded receiving element 122 or a first threaded elongate member 120 of a first elevation adjustment unit. Thus, the actuator actuates an elevation adjustment of the second segment 106 so that the second segment 106 reaches the lowest possible position.

Furthermore, in 804 control of elevation of a connecting segment 608, comprising an outer part 332 and an inner part 330 attached to an arm 610, which may be telescopic, of the elevating column 606 to a highest possible position with a second actuator, such as a second electrical motor, e.g. a Permanent-magnet Direct Current (PMDC) motor or a Brushless Direct Current (BLDC) motor, is performed. A second control signal is sent from a control unit, which has received information from position sensors, to the second actuator. The second actuator actuates a rotational movement of either a second threaded receiving element 422 or a second threaded elongate member 420 of a second elevation adjustment unit. Thus, the second actuator actuates an elevation adjustment of the connecting segment 608 so that the connecting segment 608 reaches a highest possible position.

Moreover, in 806, rotation of the outer part 332 horizontally around the inner part 330 until an arm 610, which may be telescopic, of the apparatus is positioned on top of a base 602 of the apparatus, is performed. Optionally, in 808, control of elevation of the connecting segment 608 by lowering it until the arm 610 is positioned in a locking position, such as in a hollow space of the base 602, is performed. With the use of this method, a compact size during transportation is enabled. Furthermore, the mobile X-ray apparatus may be easy to transport due to e.g. compact size and increased visibility.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. The present disclosure has been described above with reference to specific embodiments. However, other embodiments than the above described are equally possible within the scope of the disclosure. Different method steps or a different order thereof than those described above may be provided within the scope of the disclosure. The different features and steps of the disclosure may be combined in other combinations than those described. The scope of the disclosure is only limited by the appended patent claims.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A mobile X-ray apparatus comprising:
    a first segment of an elevating column, the first segment having a first end and an opposite second end, the first end arranged at a base of the X-ray apparatus;
    a second segment of the elevating column, the second segment having a first end and an opposite second end, wherein the first end of the second segment is arranged relative to the second end of the first segment such that the first and second segments can at least partially overlap within the elevating column and such that the second segment is moveable relative to the first segment;
    a first elevation adjustment unit comprising:
        a first threaded elongate member fixed at one of said first or second segments, and
        a first threaded receiving element arranged at the other of said first or second segments, the first threaded receiving element matingly engaged with said threaded elongate member for elevation adjustment of said column; and
    a second elevation adjustment unit configured to adjust the elevation of a connecting segment that is connected to an arm of an X-ray tube by moving the connecting segment radially outside and along said second segment of the elevating column, wherein at least a part of said connecting segment is located radially outside the second segment, and wherein the second elevation adjustment unit is configured to move the connecting segment relative to the second segment independently of the elevation adjustment applied by the first elevation adjustment unit to the second segment.

2. The mobile X-ray apparatus according to claim 1, wherein the arm of the X-ray tube that is connected to the connecting segment is a telescopic arm.

3. The mobile X-ray apparatus according to claim 1, wherein the first elevation adjustment is configured such that the second segment can be moved in a first direction while the second elevation adjustment unit is configured to move the connecting segment in an opposite direction with respect to the first direction.

4. The mobile X-ray apparatus according to claim 1, wherein said connecting segment comprises:
    an outer part connected to said arm, and
    an inner part connected to said moveable second segment, wherein said outer part is rotatable horizontally around said inner part.

5. The mobile X-ray apparatus according to claim 1, wherein said second segment is positioned in its lowest position and said connecting segment is positioned at the top of said moveable second segment during transportation of said apparatus.

6. The mobile X-ray apparatus according to claim 1, wherein the second elevation adjustment unit comprises:
a second threaded receiving element arranged at one of said second segment and said connecting segment, and
at least a second threaded elongate member fixed at the other of said second segment and said connecting segment, the second threaded elongate member matingly engaged with said second threaded receiving element, wherein said first elevation adjustment unit is adapted to adjust the elevation of said moveable second segment and said second elevation adjustment unit is adapted to adjust the elevation of said connecting segment.

7. The mobile X-ray apparatus according to claim 6, wherein an elevation adjustment performed by said first elevation adjustment unit is actuated by a first electrical motor connected to one of said first threaded receiving element and said first threaded elongate member, and an elevation adjustment performed by said second elevation adjustment unit is actuated by a second electrical motor preferably positioned inside said moveable second segment and connected to one of said second threaded receiving element and said second threaded elongate member.

8. The mobile X-ray apparatus according to claim 7, further including:
a control unit configured to
receive information from position sensors,
calculate a first and a second amount of elevation adjustment,
control said second electrical motor to make said second elevation adjustment unit move said connecting segment to an elevation depending on said second amount of elevation adjustment, and
control said first electrical motor to make said first elevation adjustment unit move said second segment to an elevation depending on said first amount of elevation adjustment.

9. The mobile X-ray apparatus according to claim 8, wherein one of said first and a second amount of elevation adjustment is in a first direction and the other of said first and a second amount of elevation adjustment is in a negative direction.

10. The mobile X-ray apparatus according to claim 6, wherein said second threaded elongate member has a first end and an opposite second end and wherein said second threaded elongate member is positioned outside and in parallel with said second segment so that said first end of said second threaded elongate member is positioned at said first end of said second segment and said second end of said second threaded elongate member is positioned at said second end of said second segment.

11. The mobile X-ray apparatus according to claim 10, wherein said first threaded elongate member has a first end and an opposite second end and wherein said first threaded elongate member is positioned inside one of said first and second segments so that said first end of said first threaded elongate member is positioned at said first end of said first or second segment and said second end of said first threaded elongate member is positioned at said second end of said first or second segment.

12. The mobile X-ray apparatus according to claim 11, wherein a u-shaped profile is attached to and positioned inside one of said first and second segments and wherein said first threaded receiving element is fixed to said u-shaped profile.

13. The mobile X-ray apparatus according to claim 12, wherein said second and first threaded receiving elements comprise at least one of nuts, nut-shaped elements, or elongated hollow rods with internal threads.

14. The mobile X-ray apparatus according to claim 13, wherein a pitch or lead of an internal thread of said second threaded receiving element and an external thread of said second threaded elongate member is larger than a pitch or lead of an internal thread of said first threaded receiving element and an external thread of said first threaded elongate member.

15. The mobile X-ray apparatus according to claim 14, wherein said pitch or lead of said thread of said second threaded receiving element and said second threaded elongate member is at least two times larger than said pitch or lead of said thread of said first threaded receiving element and said first threaded elongate member.

16. The mobile X-ray apparatus according to claim 7, wherein at least one of said second and first threaded elongate members has automatic braking properties.

17. The mobile X-ray apparatus according to claim 1, wherein said base is provided with a recess and wherein said first end of said first segment is fixed to said base at said recess and recessed into said recess.

18. The elevating column according to claim 1, wherein a first electrical motor is fixed to said base, located at a distance from said elevating column and connected to said first elevation adjustment unit with a chain, a cable or a belt.

19. The mobile X-ray apparatus according to claim 1, wherein at least one of said second and first segments comprise four complete walls arranged in a rectangular or square formation cross-sectionally.

20. The mobile X-ray apparatus according to claim 1, wherein said elevating column is operated without a counterweight.

21. The mobile X-ray apparatus according to claim 1, wherein an overlap of said second and first segments, when said column is set to a highest position, is within 10-20 cm.

22. The mobile X-ray apparatus according to claim 1, wherein a ratio between an overlap of said second and first segments, when said column is set to a highest position, and a maximum height above the floor of said column is below 0.1.

23. The mobile X-ray apparatus according to claim 1, wherein a length of said second segment and a length of said first segment are selected so that a span between a lowest possible position and a highest possible position of said elevating column is optimized and at least 1.5 m.

24. A method of controlling elevation of a mobile X-ray apparatus, the method comprising:
receiving information from position sensors;
sending a first control signal to a first electrical motor operably connected to a first elevation adjustment unit in order to control the first elevation adjustment unit, the first elevation adjustment unit being used to control an elevation of an elevating column of the mobile X-ray apparatus, the elevating column comprising a first segment and a second segment, wherein the first electrical motor adjust affects first elevation adjustment unit via by actuating a rotational movement of at least one of:
a first threaded elongate member of the first elevation adjustment unit, the first threaded elongate member being fixed at one of said first or second segments, or a first threaded receiving element of the first elevation adjustment unit, the first threaded receiving element being arranged at the other of said first or second segments of the elevating column, the first threaded receiving element matingly engaged with said threaded elongate member for elevation adjustment of said column; and sending a second control signal to a second electrical motor operably connected to a second elevation adjustment unit in order to control the second elevation adjustment unit, wherein the second elevation adjustment unit controls an elevation of a connecting segment of the mobile X-ray apparatus, the connecting segment is connected to an arm of an X-ray tube, the second elevation adjustment unit moves the connecting segment radially outside and along said second segment of the elevating column, and the second elevation adjustment unit moves the connecting segment relative to the second segment independently of the elevation adjustment applied by the first elevation adjustment unit to the second segment.

25. The method of claim 24, wherein said the first elevation adjustment unit and the second elevation adjustment unit are controlled simultaneously.

26. A method of preparing a mobile X-ray apparatus for transport, the method comprising:

sending a first control signal to a first electrical motor operably connected to a first elevation adjustment unit in order to control the first elevation adjustment unit such that a second segment of an elevating column of the mobile X-ray apparatus is moved to a lowest position relative first segment of the elevating column, wherein the first electrical motor adjust affects first elevation adjustment unit via by actuating a rotational movement of at least one of:

a first threaded elongate member of the first elevation adjustment unit, the first threaded elongate member being fixed at one of said first or second segments, or a first threaded receiving element of the first elevation adjustment unit, the first threaded receiving element being arranged at the other of said first or second segments of the elevating column, the first threaded receiving element matingly engaged with said threaded elongate member for elevation adjustment of said column; and sending a second control signal to a second electrical motor operably connected to a second elevation adjustment unit in order to control the second elevation adjustment unit such that an elevation of a connecting segment of the mobile X-ray apparatus is moved to a highest position, wherein the connecting segment is connected to an arm of an X-ray tube, the second elevation adjustment unit moves the connecting segment radially outside and along said second segment of the elevating column, and the second elevation adjustment unit moves the connecting segment relative to the second segment independently of the elevation adjustment applied by the first elevation adjustment unit to the second segment; and rotating an outer part the connecting segment horizontally around an inner part of the connecting segment until said arm is positioned on top of a base of said mobile X-ray apparatus.

* * * * *